United States Patent [19]

Baldinger et al.

[11] Patent Number: 4,914,125
[45] Date of Patent: Apr. 3, 1990

[54] (S)-EMOPAMIL FOR THE TREATMENT OF MIGRAINE

[75] Inventors: Verena Baldinger, Heidelberg; Liliane Unger, Ludwigshafen; Laszlo Szabo, Heidelberg, all of Fed. Rep. of Germany

[73] Assignee: Knoll AG, Ludwigshafen, Fed. Rep. of Germany

[21] Appl. No.: 375,996

[22] Filed: Jul. 6, 1989

[30] Foreign Application Priority Data

Jul. 9, 1988 [DE] Fed. Rep. of Germany ....... 3823378

[51] Int. Cl.$^4$ ............................................ A61K 31/275
[52] U.S. Cl. ..................................................... 514/520
[58] Field of Search ......................................... 514/520

[56] References Cited

FOREIGN PATENT DOCUMENTS 0147707 3/1987 European Pat. Off. .

OTHER PUBLICATIONS

European Journal of Pharmacology, D. De Wied, vol. 106, 1984, 215, (1985).
Drugs, vol. 31, 149 (1986) Focus on Betaxolol and Tioconazole, D. S. Houston and P. M. Vanhoutte.
Annual Reports in Medicinal Chemistry, vol. 22, Denis M. Bailey, pp. 41–50.
Drugs of Today, vol. 24, No. 2, Feb. 1988, Greenberg et al.
Drugs, Focus on Bezafibrate and Sulbactam/Ampicillin, Jun. 1987, vol. 33, No. 6 (pp. 531–635).
The Journal of the American Medical Association, Nov. 11, 1983, Preliminary Communication, Capt. Glen D. Solomon et al.
Neurology, Official Journal of the American Academy of Neurology, Jul. 1984, vol. 34, No. 7, p. 973 (1984).

*Primary Examiner*—Stanley J. Friedman
*Attorney, Agent, or Firm*—Oblon, Spivak, McClelland, Maier & Neustadt

[57] ABSTRACT

The use of (S)-emopamil and the salts thereof for the treatment of migraine is described.

1 Claim, No Drawings

(S)-EMOPAMIL FOR THE TREATMENT OF MIGRAINE

The present invention relates to the use of (S)-emopamil for the preventive and acute treatment of migraine.

EP-A 147,707 describes 2-isopropyl-5-(methylphenethylamino)-2-phenylvaleronitrile (called emopamil hereinafter) and the enantiomers thereof, as well as the use thereof for controlling diseases, including oxygen deficiency states of the brain.

It is known that, apart from its calcium-antagonistic action, verapamil additionally has a serotoninantagonistic action which, however, is weak by comparison with known serotonin antagonists [J. E. Taylor and F. V. DeFeudis, Eur. J. Pharmacol. 106 (1985), 215–216]. It is furthermore known that serotonin is of great importance in the pathogenesis of migraine [D. S. Houston and P. M. Vanhoutte, Drugs 31 (1986), 149–163; G. Johnson, Ann. Rep. Med. Chem. 22 (1987), 41–50]. It may be assumed that there will be an additive, if not in fact a potentiating, effect of antagonism of calcium and of serotonin in migraine.

Clinical investigations have shown that prophylactic use of the calcium antagonist verapamil represents an effective therapy of classical and atypical migraine as well as cluster headaches [D. A. Greenberg, Drugs of Today 24 (1988), 133–142; K. J. Tietze et al., Drugs 32 (1987), 531–538].

Optimal results were achieved only after treatment had lasted one month [G. D. Solomon et al., JAMA 250 (1983), 2500–2502; H. G. Markley et al., Neurology 34 (1984), 973–976], which is probably attributable to the low acute availability of verapamil in the brain and/or to a less pronounced serotonin antagonism.

We have found that (S)-emopamil and the physiologically tolerated salts thereof have an antiserotonin action which reaches the potency of known serotonin antagonists and exceeds by a multiple that of the comparison compound verapamil. In addition, it has been shown by means of the brain uptake index (BUI) that the verapamil derivative (S)-emopamil passes the blood/brain barrier more rapidly and in considerably larger amounts than does verapamil.

The superior serotonin-antagonistic action of (S)-emopamil can be shown, for example, by the inhibition of the increase in blood pressure induced by serotonin in the pithed rat on intravenous administration:

Male Sprague-Dawley rats weighing 200 to 280 g are subjected, under amobarbital anesthesia (120 mg/kg body weight i.p.), to cannulation of the carotid artery and jugular vein and to bilateral division of vagus and sympathetic nerves, and the animals are connected to a breathing pump. The pithing is carried out by a rod through the orbit. In control animals which have not been treated, injections of 0.0215 mg/kg serotonin i.v. increase the mean arterial pressure from $53 \pm 0.6$ mm Hg to $80 \pm 1.2$ mm Hg (n = 95). The criterion of an action of a substance is the relative inhibition (δ-%) of the increase in blood pressure induced by serotonin (δmm Hg). The quantitative evaluation is by analysis of the linear regression (y = a+b x) between log dose (mg/kg) and relative inhibition (δ%) of the increase in blood pressure due to serotonin. For comparisons, the ED 50% was calculated as the dose which inhibits the increase in blood pressure due to serotonin by 50%.

The results were as follows:

|  | Ed 50% |
|---|---|
| Verapamil | 0.36 mg/kg |
| (S)-Emopamil | 0.02 mg/kg |

The results show that (S)-emopamil has a serotoninantagonistic action in the pithed rat after i.v. administration which is 18 times that of verapamil.

On oral administration, (S)-emopamil is superior to the comparison compound verapamil in the serotoninantagonistic action by a factor of 4.6.

The good cerebral availability (BUI values) of (S)-emopamil by comparison with verapamil was determined by injection into the common carotid artery of the anesthetized rat after a single passage through the cerebral capillaries [method: W. H. Oldendorf, Brain Research 24 (1970), 372–376]. The [$^{14}$C]-labeled test substances were administered in HEPES-buffered Ringer solutions (pH=7.35) together with [$^3$H]-labeled water as internal standard. The calculated BUI values indicate the cerebral uptake as a percentage of the water uptake.

The following BUI values were found:

| Verapamil | 40.6% |
|---|---|
| (S)-Emopamil | 110% |

By reason of its excellent serotonin-antagonistic action and its high cerebral availability, (S)-emopamil is particularly suitable for the prophylaxis and for the treatment of episodes of primary headaches of every type, especially of classical and atypical migraine, cluster headaches and mixed forms thereof.

(S)-Emopamil can be administered in a conventional manner orally, parenterally (intravenously, intramuscularly, subcutaneously) or rectally.

Examples of suitable physiologically tolerated acid are: hydrochloric acid, hydrobromic acid, sulfuric acid, phosphoric acid, acetic acid, maleic acid, lactic acid tartaric acid, citric acid and fumaric acid.

The dosage depends on the age, condition and weight of the patient and on the mode of administration. As a rule, the daily dose of active substance is from about 1 to 50 mg/kg body weight on oral and rectal administration and from about 0.1 to 5 mg/kg body weight on parenteral administration.

(S)-Emopamil can be used in conventional solid or liquid pharmaceutical forms for administration, for example as tablets, film-coated tablets, sugar-coated tablets, capsules, powders, granules, suppositories or solutions. These are prepared in a conventional manner. The active substances can be processed in this connection with the conventional pharmaceutical aids such as tablet binders, fillers, preservatives, tablet disintegrants, flow-regulating agents, plasticizers, wetting agents, dispersants, emulsifiers, suppository bases, solvents, retardants and/or antioxidants (cf. H. Sucker et al. Pharmazeutische Technologie [Pharmaceutical Technology], Thieme-Verlag, Stuttgart, 1978]. The forms for administration obtained in this way normally contain the active substance in an amount of from 1 to 99 percent by weight.

The Examples which follow illustrate the invention.

EXAMPLE 1

Tablets of the following composition were produced in a tableting machine in a conventional manner:

| | |
|---|---|
| 40 mg | (S)-emopamil hydrochloride |
| 120 mg | corn starch |
| 13.5 mg | gelatin |
| 45 mg | lactose |
| 2.25 mg | Aerosil ® (chemically pure silica in submicroscopically fine distribution) |
| 6.75 mg | potato starch (as 6% strength paste). |

EXAMPLE 2

Sugar-coated tablets of the following composition are produced in a conventional manner:

| | |
|---|---|
| 20 mg | (S)-emopamil hydrochloride |
| 60 mg | core composition |
| 60 mg | sugar-coating composition |

The core composition comprises 9 parts of corn starch, 3 parts of lactose and 1 part of Luviskol. VA 64 (60:40 vinylpyrrolidone/vinyl acetate copolymer, cf. Pharm Ind. 1962, 586). The sugar-coating composition comprises 5 parts of sucrose, 2 parts of corn starch, 2 parts of calcium carbonate and 1 part of talc. The sugar-coated tablets produced in this wire are then provided with an enteric coating.

EXAMPLE 3

10 g of (S)-emopamil hydrochloride are dissolved in 5000 ml of water with the addition of NaCl, and the pH is adjusted to 6.0 with 0.1 N NaOH so that a solution which is isotonic with blood is produced. 5 ml portions of this solution are dispensed into ampoules and sterilized.

EXAMPLE 4

Suppositories of the following composition are produced in a conventional manner:

| | |
|---|---|
| 100 mg | (S)-emopamil hydrochloride |
| 40 mg | Aerosil ® |
| 1900 mg | hard fat. |

We claim:
1. A method of treating migraine in patients suffering therefrom, which comprises administering to said patients an effective amount of (S)-emopamil or a physiologically acceptable salt thereof.

* * * * *